United States Patent
Mbachu et al.

(10) Patent No.: US 7,128,867 B2
(45) Date of Patent: *Oct. 31, 2006

(54) METHODS FOR MONITORING RESIN-LOADING OF WOOD MATERIALS AND ENGINEERED WOOD PRODUCTS

(75) Inventors: Reginald A. Mbachu, Eugene, OR (US); Tyler G. Congleton, Eugene, OR (US)

(73) Assignee: Dynea Chemicals Oy, Eugene, OR (US)

(*) Notice: Subject to any disclaimer, the term of this patent is extended or adjusted under 35 U.S.C. 154(b) by 0 days.

This patent is subject to a terminal disclaimer.

(21) Appl. No.: 11/008,097

(22) Filed: Dec. 10, 2004

(65) Prior Publication Data
US 2005/0101024 A1 May 12, 2005

Related U.S. Application Data

(63) Continuation of application No. 10/338,069, filed on Jan. 7, 2003, now Pat. No. 6,846,447, which is a continuation-in-part of application No. 10/294,296, filed on Nov. 14, 2002, now Pat. No. 6,846,446.

(51) Int. Cl.
*B29C 45/76* (2006.01)
(52) U.S. Cl. ............... 264/406; 264/410; 264/488; 264/492; 264/40.1

(58) Field of Classification Search .......... 264/406
See application file for complete search history.

(56) References Cited

U.S. PATENT DOCUMENTS 3,196,072 A * 7/1965 Wirtz ................. 162/198
5,619,038 A * 4/1997 Parigi et al. ......... 250/339.12

* cited by examiner

*Primary Examiner*—Christina Johnson
*Assistant Examiner*—Monica A Huson
(74) *Attorney, Agent, or Firm*—Shanley and Baker

(57) ABSTRACT

Process for calibration of spectroscopic instrumentation for non-invasive monitoring of resin-loading of furnish-type wood materials, such as particles or fibers for particleboard or medium density fiberboard, respectively. Selection of ranges of wavelengths within a 350 nm to 2500 nm region by providing selection of spectrometers and sensors for wavelength ranges of 350–1000 nm, 1000 to 1800 nm, 1000 to 2500 nm, and 400 to 2200 nm, for use by engineered-wood manufacturing installations. Resin-loaded wood material is exposed to selected VIS/NIR energy and monitored as it moves on-line in relation to calibrated spectroscopic instrumentation; a sensor collects non-absorbed radiation energy reflected by the wood materials. Measurements are processed, in relation to pre-established calibration data, to determine whether the resin-loading is within manufacturing objectives; monitoring and feedback are used to maintain desired specifications.

10 Claims, 8 Drawing Sheets

METHODS FOR MONITORING RESIN-LOADING OF WOOD MATERIALS AND ENGINEERED WOOD PRODUCTS

RELATED APPLICATION

This is a continuation of application Ser. No. 10/338,069 filed Jan. 7, 2003 now U.S. Pat. No. 6,846,447 which is a continuation-in-part of Ser. No. 10/294,296 filed Nov. 14, 2002 now U.S. Pat. No. 6,846,446.

INTRODUCTION

The present invention relates to methods and apparatus for monitoring resin-loading of wood materials during assembly for manufacture of engineered wood product. More specifically, this invention is concerned with calibration and use of spectroscopic instrumentation for quantitatively measuring resin-loading during on-line assembly of composite wood product; and, maintaining that resin-loading within manufacturing standards, in particular, during assembly of particleboard (PB) and medium-density fiberboard (MDF).

OBJECTS OF THE INVENTION

A primary object provides for calibrating spectroscopic instrumentation for accurate and prompt measurement of resin loading during assembly of wood materials prepared for manufacture of composite wood product.

A related object provides for calibrating use of spectrometers using selected wavelength ranges within the full visual (VIS) and near-infrared (NIR) wavelength region of electromagnetic radiation.

An important object provides for monitoring resin-loading of wood particulate and fiber materials during on-line assembly, respectively, of particleboard (PB) and medium-density fiberboard (MDF).

A specific object is to provide on-line measurement of resin-loaded wood materials as assembled prior to heat and pressure bonding treatment.

A further object provides for feedback of resin-loading data to maximize continuing on-line assembly within manufacturing standards and to optimize resin usage.

The above objects and other contributions of the invention are considered in more detail in describing the invention in relation to the accompanying drawings.

DETAILED DESCRIPTION OF THE INVENTION

Contributions of the invention involve uncovering opportunities for potential improvement in the assembly and manufacture of engineered wood product. Recognizing that producing quality composite wood product requires a consistent rate of application of resin was a major factor in determining that consistency in resin-loading can best be achieved by quantitative-analyses during assembly of the raw-wood material. And, also, concluding that in order to ensure product homogeneity, minimize out-of specification product, and optimize adhesive resin use, accuracy in measuring resin-loading should be carried-out while the wood material is traveling during in-line assembly.

Specific embodiments are described working with furnish-type wood-material. An adhesive resin in liquid form is atomized and directed into a chamber forming a fluidized bed for in-line movement of the wood material; and, resin application is carried out during that movement in the fluidized bed while moving at an in-line assembly rate. Specific examples of wood material include particulate wood for manufacture of particleboard (PB) and wood fibers for assembly of medium-density fiberboard (MDF). Resin-loading of the wood material is monitored following resin application in an assembly line, prior to heat and pressure bonding treatment to form commercial engineered wood product.

The above procedures provide early on-line detection of out-of-specification material, if any; and, in addition, the invention provides for adjustment of resin-loading, if any is required, to be carried out promptly to bring the resin-loading within manufacturing specifications. Promptly maintaining desired manufacturing specifications minimizes or eliminates losses in material and production rate.

It is significant that non-invasive on-line monitoring of resin-loading takes place without disturbing furnish-like wood materials during assembly. Resin measurement involves use of spectroscopic measuring instrumentation utilizing electromagnetic radiation which is absorbed by the wood material. Further, accurate measurement of resin-loading is dependent on calibration, as disclosed herein, of that instrumentation.

The term "resin-loading" is used interchangeably herein with "resin content"; and, resin-loading of particulate and fiber "furnish" is measured and indicated as a weight percentage in relation to the weight of the wood material.

For resin-loading of particleboard (PB), liquid resin is atomized for application to sawdust-type wood particulate. After non-invasive measurement of resin content, the resin-loaded particulate is then subjected to heat and pressure, in a press layout which cures the resin resulting in bonding, to produce an extended-surface-area mat, which can later be cut into commercial sizes. The present non-invasive and continuing measuring contributions are particularly advantageous for manufacturing installations carrying out bonding in a continuous-in-line press.

Figure 1:
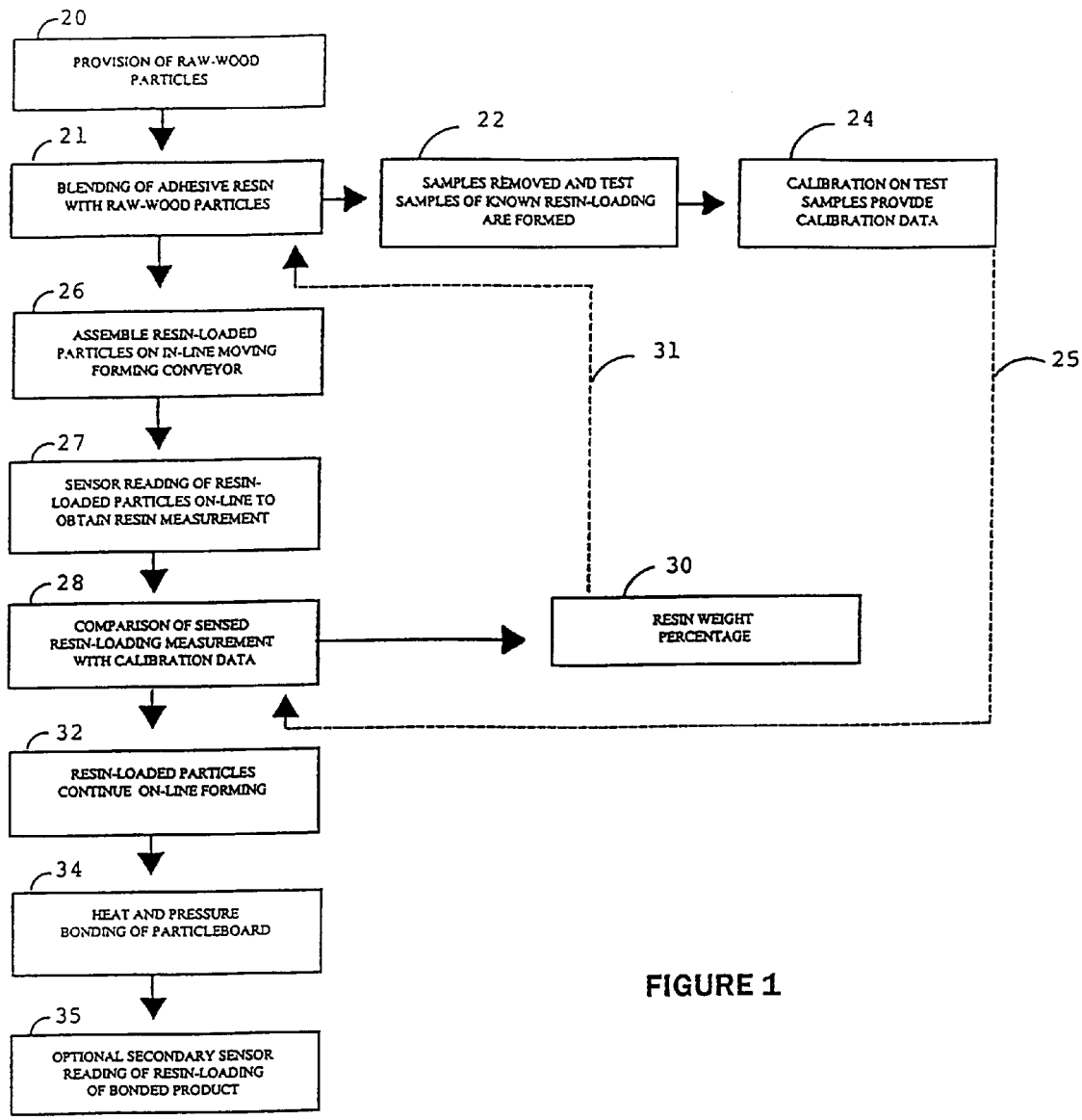
FIG. 1 is a block diagram for describing on-line assembly and processing in accordance with the invention for production of particleboard (PB)

In FIG. 1, raw-wood particulate for a particleboard (PB) embodiment is supplied at station 20; and, directed to station 21 for resin-loading with adhesive resin. Resin-loading can be carried out by feeding wood particulate into an elongated rotating chamber, or drum-like structure, extending for longitudinal travel in the assembly-line direction. The liquid resin is atomized and sprayed into the chamber to create a fluidized bed of resin; the particulate moves through that fluidized bed toward assembly.

Relating the material of interest to the measuring technique for quantitative analyses, it was discovered that, spectroscopically, resin-loading is related in a linear manner to absorption of radiation within a selected electromagnetic radiation wavelength range; and, calibration of spectroscopic instrumentation could accordingly be verified. That calibration can be initiated in an assembly line at station 22.

During calibration, in summary, wood materials of the type to be assembled are selected and accurately-predetermined resin-content reference-source test-samples are established. With furnish-type wood material, resin-loaded determinations are established by making static chemical-test measurements of the test sample materials for accurate resin-loaded weight in relation to weight of furnish. Preferably, reference-source test-samples, for calibration purposes, are resin-loaded in an incrementally progressive manner; such as: zero percent, about four percent, about eight percent, and above about twelve percent.

Calibration of spectroscopic instrumentation, within a selected range of visible (VIS) and near infrared (NIR) irradiation is carried out at station 24; calibration steps are described in more detail and graphically presented in relation to later FIGS. It has been found that the wavelength bands for moisture-content (MC) of both the woodland the resin do not effect accurate measurement of resin content; and, MC wavelength bands can be removed when the instrumentation is used to measure resin content. It should be noted that non-absorbed energy reflected by the wood materials is used to measure resin content. Calibration data, from the instrumentation used for measuring resin content, is directed from station 24 over interrupted-line 25, for use in the assembly line for the wood materials.

At station 26 in the assembly line, resin-loaded particulate is supported on an in-line conveyance system for continuing assembly of a mat of particulate, which is moving toward ultimate bonding by heat and pressure. Non-invasive capabilities for measuring of resin-loading are significantly important during assembly of wood particulate. VIS/NIR spectroscopic instrumentation for carrying out continuing non-invasive measurement is located at station 27.

A lamp with full-spectrum-light is used to illuminate the wood materials; the "red" portion of that light is absorbed by the resin. Non-absorbed radiation energy, reflected by the wood materials, is measured by the instrumentation-sensor. The sensor is positioned a selected distance from the resin-loaded materials for laboratory determination of a calibration model and, also, for calibration of instrumentation being used on an assembly line. The sensor is placed above the moving materials. The illuminated and VIS/NIR irradiation covers a selected area of about three to about twenty four square inches; VIS/NIR radiation is selected in a wavelength range, made available by the invention, which penetrates the resin-loaded blend by about two to five mm.

The return reflected VIS and NIR energy is collected fiber-optically and is computer processed at station 28 to enable graphical presentation of absorbed radiation based on reflected non-absorbed radiation; instrumentation calibration data for measuring resin-loading is received, as referred to above, over interrupted-line 25 from station 24. That measurement of resin-loaded percentage weight is indicated at station 30. During production, adjustment of resin-loading percentage weight, if any is required, can be directed, manually or automatically, over interrupted-line 31 to resin-loading station 21. The rate of resin-input can be adjusted, or the assembly line-speed can be adjusted, in order to maintain uniform resin-loading; preferably the rate of resin-input is utilized.

The resin-loaded particulate at station 32 continues toward bonding at station 34. If desired, a secondary sensor can be positioned at station 35, after heat and pressure treatment, to measure resin-loading of the bonded product; station 35 can provide added confirmation that the resin bonded product is within desired manufacturing objectives.

Figure 2:
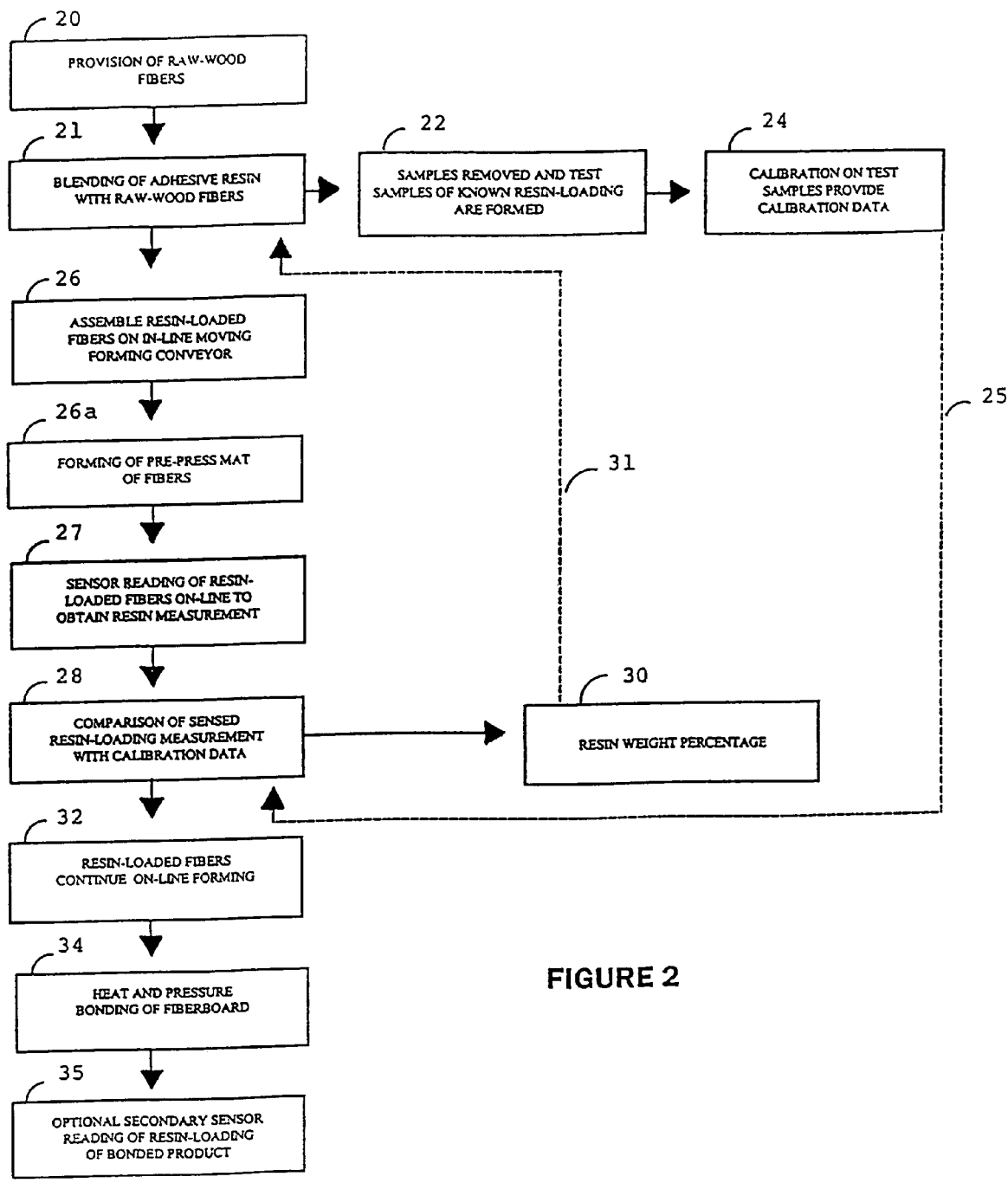
FIG. 2 is a block diagram for describing on-line assembly and processing in accordance with the invention for production of medium-density fiberboard (MDF)

Referring to FIG. 2 for assembly of MDF, a number of the method steps, as described above in relation to PB remain substantially the same for production of MDF. One difference of note for raw-wood fibers has significance. Prior to on-line calibrated monitoring of resin content, raw-wood fibers are resin-loaded. At station 26(a) of FIG. 2, a pre-press compacting of those fibers is used. Otherwise, because of the light-weight of raw-wood fibers, and the tendency to accumulate with intermediate air spacing, accurate measurements for uniformity of resin-content, throughout, can be more difficult because of the accumulated fiber height. The compacting of fibers for resin-loading measurement purposes does not require heat, and, utilizes minimum pressure to achieve desired compaction.

Other than that pre-bonding compaction of fibers, any differences in measuring resin-content between the furnish-like materials of wood particulate and wood fibers are inconsequential for purposes of carrying out the measuring methods of the invention, although the finished composite wood products are significantly different. Various types of wood for particulate for PB, or for fiber for MDF, can be used when carrying out measurements in accordance with the invention.

During calibration in a lab or on-line, accurate resin-loaded reference-source test-samples are used for establishing a calibration curve for the instrumentation. For spectroscopic quantitative analyses, a relationship between content of the material and transmittal or absorption of the radiation is the basis calibration of instrumentation. It was determined that a linear relationship exists between absorption of radiation and the amount of resin-content; and, that is used for calibration of the instrumentation. The calibration equipment of FIG. 3 to be described can be adapted for use in a lab or on-line.

Figure 3:
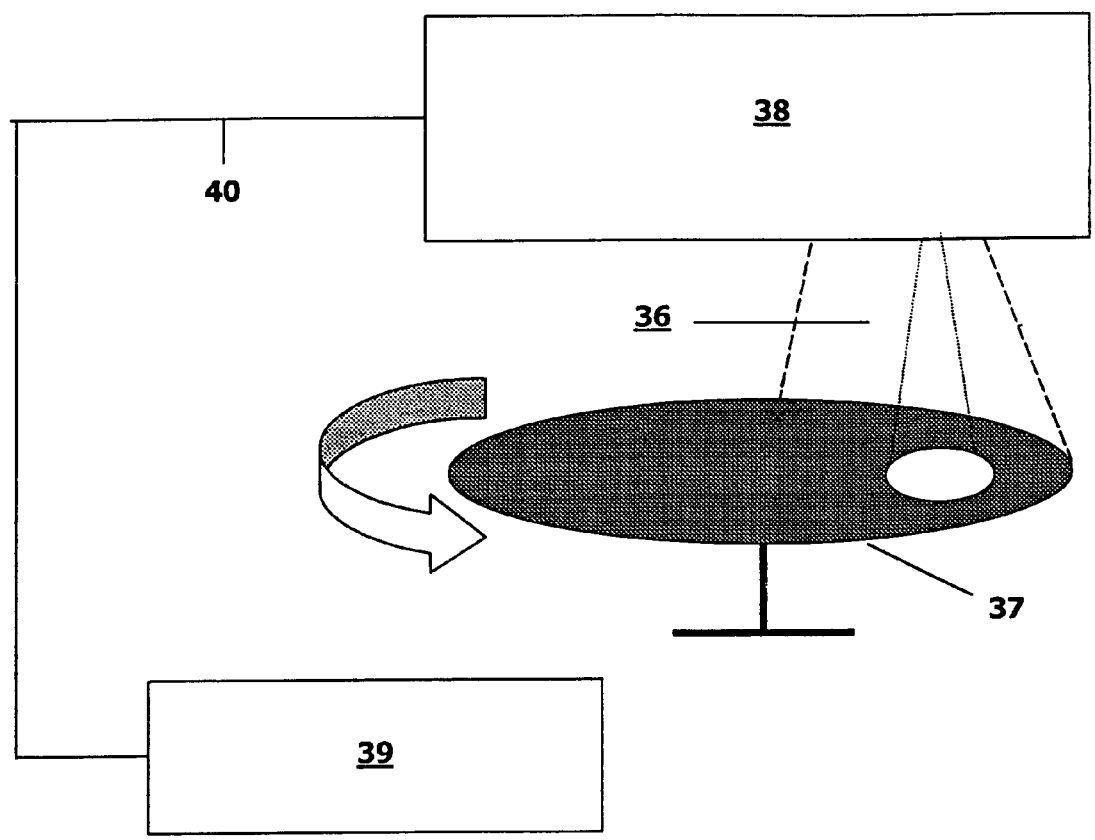
FIG. 3 is a schematic perspective view of apparatus for describing calibration steps, in accordance with the invention, for spectroscopic instrumentation.

A rotatable turntable 37, schematically illustrated in FIG. 3, is actuated so as to simulate an on-line assembly travel rate. Reference-source test-samples are supported on turntable 37, which is rotated to simulate movement of in-line material to be monitored. Calibration involves establishing the relationship between observance of spectral energy and the resin content; and can be carried out in the same manner for lab calibration or online calibration. However, calibration is preferably conducted for each accumulated wood material for a scheduled run of a line to be monitored since differing manufacturing specifications may apply for differing runs.

Absorption, within a selected range of VIS/NIR radiation, by the wood material is utilized. The resin-loading is determined by measuring non-absorbed VIS/NIR energy reflected by the wood material. Calibration is carried out by graphically-representing "resin content" of pre-established reference-source test-samples; based on the linear relationship of resin content to absorbed VIS/NIR. The calibration curve correlates that linear relationship, as shown graphically in later FIGS, for measurements of actual resin-loading on-line.

A unique advantage during calibration, and for on-line monitoring, is the non-invasive nature of resin-loading measuring of the furnish-type wood materials. That is, calibration of spectroscopic instrumentation, and on-line measurement of resin-loading of wood materials during assembly, can proceed without disturbing the wood materials which are resin-loaded. Of course, when on-line measurements indicate that resin-loading is not within manufacturing standards, resin-loading adjustments are made; but, again, those measurements are made without disturbing the actual assembly of furnish-type wood material.

Absorption of radiation by the resin-loaded materials can be measured by selecting a wavelength range, from the full-scale wavelength region of 350 nanometers to 2500 nanometers (nm), which provides for penetration of the wood material. A wavelength range of 400–2200 nm satisfactorily covers the above-mentioned full scale region. However, significantly, it has been discovered that acceptable standards can be maintained by other than use of full-scale, or near full-scale, wavelength regions.

It has been found that selection can be made from multiple ranges of wavelengths; an individual wavelength range can be selected from the following: (i) 350–1050 nm, (ii) 1000–1800 nm and (iii) 1000–2500 nm; those ranges and the type of sensors for measuring resin loading in each range are later tabulated herein. The resulting advantages from discovery of those multiple ranges can be important in relation to the size of composite-wood manufacturing installations.

During calibration, direct measurements are made of reference-source test samples wherein the amount of resin has been accurately pre-established. Selected peaks in the spectrum are used in calibration, which brought out that moisture content (MC) absorption wavelength band could be eliminated. That calibration data is correlated with measurements in which those samples are obtained from raw-wood material for the on-line assembly process. The apparatus of FIG. 3 can be used in a lab or for on-line calibration; an accurate linear calibration curve date is described and shown in later FIGS.

The resin-loaded wood materials are illuminated with a full visible light spectrum lamp as indicated at 36 in FIG. 3; also, a VIS/NIR source, selected from the above ranges, is mounted in sensor head 38. Reflected return energy received by sensor head 38 is transmitted to processing unit 39 by means of a fiber optic cable 40, which is attached to the sensor head, for computer processing to determine and indicate resin-content based on non-absorbed reflected radiation energy.

EXAMPLE I

Resin-loading of Particles

Example I involves VIS/NIR spectroscopic measurements to determine resin-loading of particles which are to be made into particleboard (PB). Resin-loading for calibration can be varied from 0% to above about 12%; initial moisture content (MC) can be 6%. Spectral data were collected using instrumentation and software as tabulated later herein. The instrument sensor head is connected to a fiber optic bundle. The sensor head is mounted about seven inches above the particle/resin blend. The size illumination and measurement area can be between about a three inch diameter to about a twenty inch diameter on the moving support for the test samples.

Example I was carried out using a rotary table. For calibration, test-samples having known pre-established resin contents were measured. It had been determined that resin-loading is in linear relationship with absorbed radiation of the selected wavelength range(s). The resulting measurements of the predetermined test samples establish that a linear relationship between absorbed radiation and resin-loaded percentage weights, which is the basis for the linear calibration curve shown later herein.

The turntable simulates a rate of movement on a continuous conveyor system. Although the height of the furnish was not strictly controlled in the lab embodiment, a straight edge can be used to roughly level the surface where the VIS/NIR beam contacts the furnish. The bulk of the measurement was made on 6% initial moisture content (MC) PB furnish.

Figure 4:
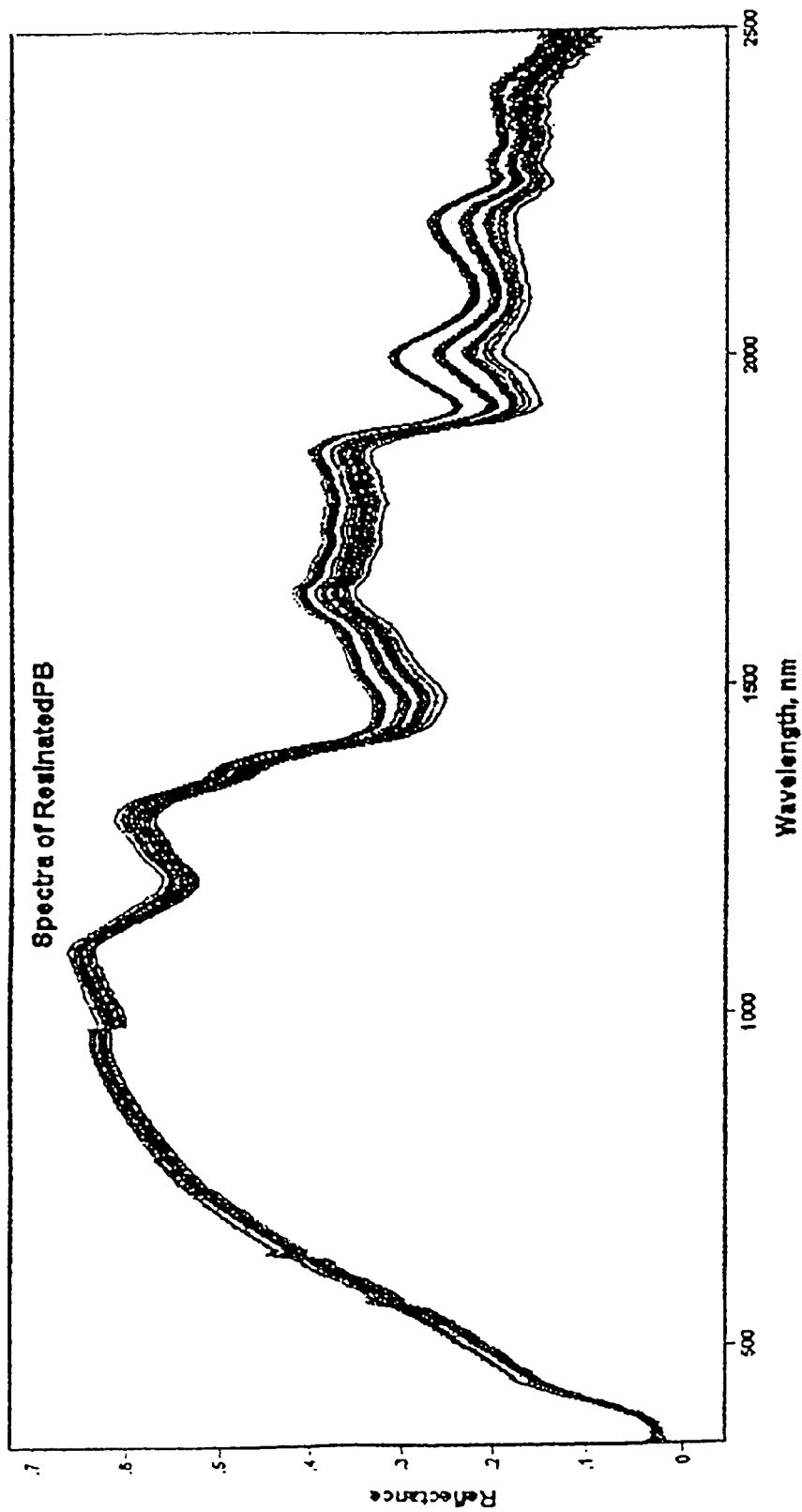
FIGS. 4 and 5 present graphical resin-loading measurement data relating to the particleboard (PB) embodiment of the invention of FIG. 1, and FIGS. 6–8 present graphical resin-loading measurement data relating to the Medium Density Fiberboard (MDF) embodiment of the invention of FIG. 2.

FIG. 4 shows the spectra obtained measuring samples at differing resin loadings for the particulate described above. The data verifies that moisture content (MC) has no significant effect on resin content measurements; measurement can be made with or without removal of the water bands. Based on measurements of actual resin-content values, a coefficient of regression of 0.9974 was obtained.

Figure 5:
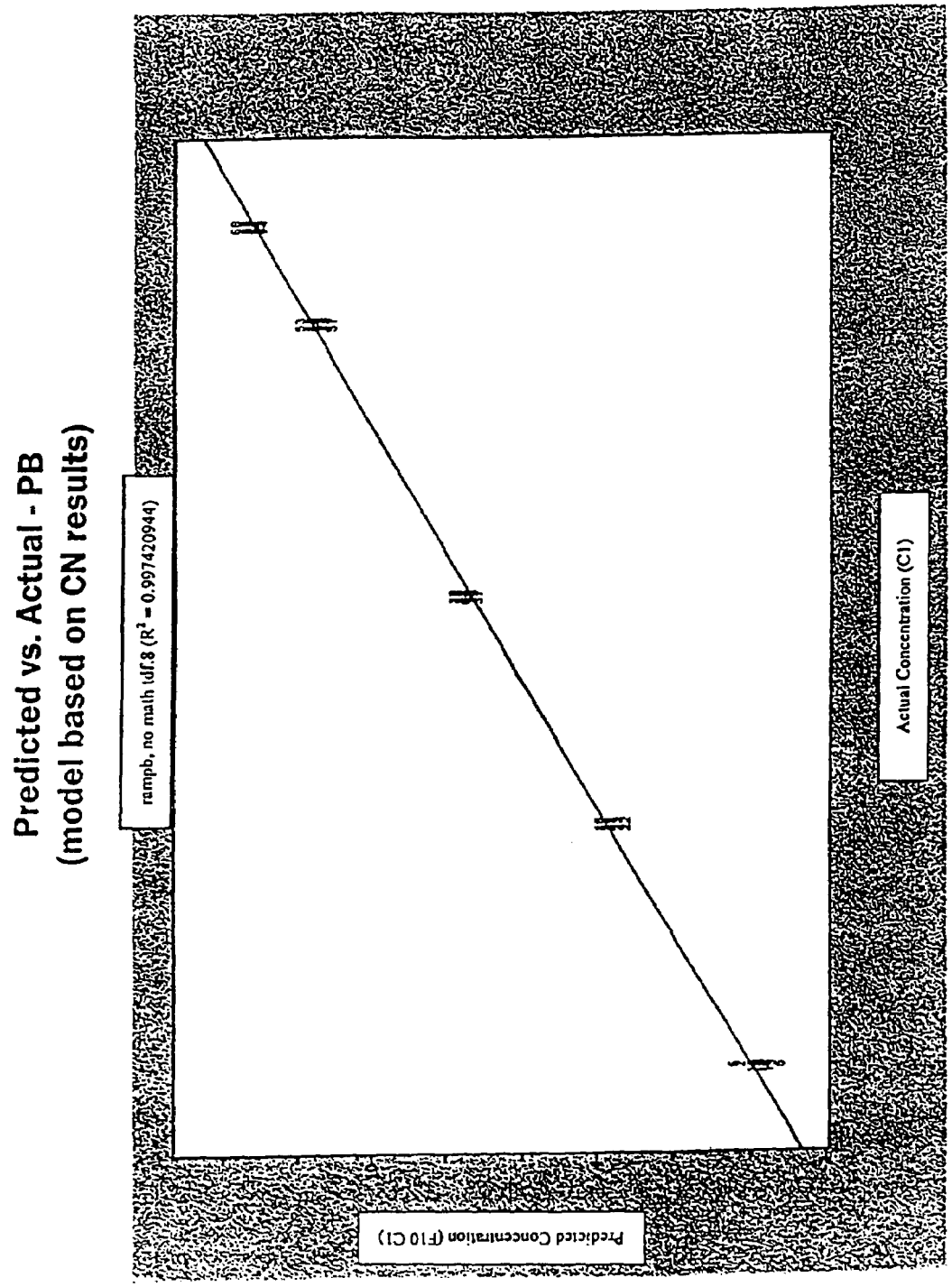

FIG. 5 shows the linear calibration curve resulting from such measurements in which resin-loading percentage weight is linearly related to absorbed radiation energy.

EXAMPLE II

Resin-loading of Fibers

Example II utilizes VIS/NIR spectroscopic instrumentation for determination of resin-loading of medium density fiberboard (MDF) fibers which are compacted as described earlier. Resin-loading was varied from zero to above about twelve percent; MC was varied from six to ten percent. Spectral data were collected with a sensor head connected to a fiber optic bundle. The sensor head was mounted at a distance of about seven inches above the compacted form. The illumination measurement area covered about a three to about a twenty square inch area. Example II was supported using a rotary turntable. A wavelength range was selected in the 350–2500 nm spectral region. Measurements again verify that moisture content has no significant effect on measurement of resin-loading.

The resin used in Example II was the same UF resin utilized in Example I. Measurements were made on compacted MDF placed on a turntable; rotation at ten rpm was established. As above noted, the turntable was rotated to simulate the travel rate of a continuous conveyor system. The bulk of the measurement was made on six percent MC wood material; but measurements were also carried-out on compacted MDF containing ten percent MC.

Resin levels were pre-established at 0%, 4%, 8% and about 12%. Atomized resin was fed into a blending chamber and applied to the wood fibers from a fluidized resin bed established in the chamber. A Carbon-Nitrogen (CN) static chemical analyzer was used to establish actual resin content of referenced-source test-samples. The sensor head was suspended above the pre-press form at a distance of about seven inches; fiber height of the pre-press forms was not closely monitored, which is similar to production conditions. Non-absorbed reflected VIS/NIR spectral data were obtained and processed by computer to provide resin-content percentage weight.

Figure 6:
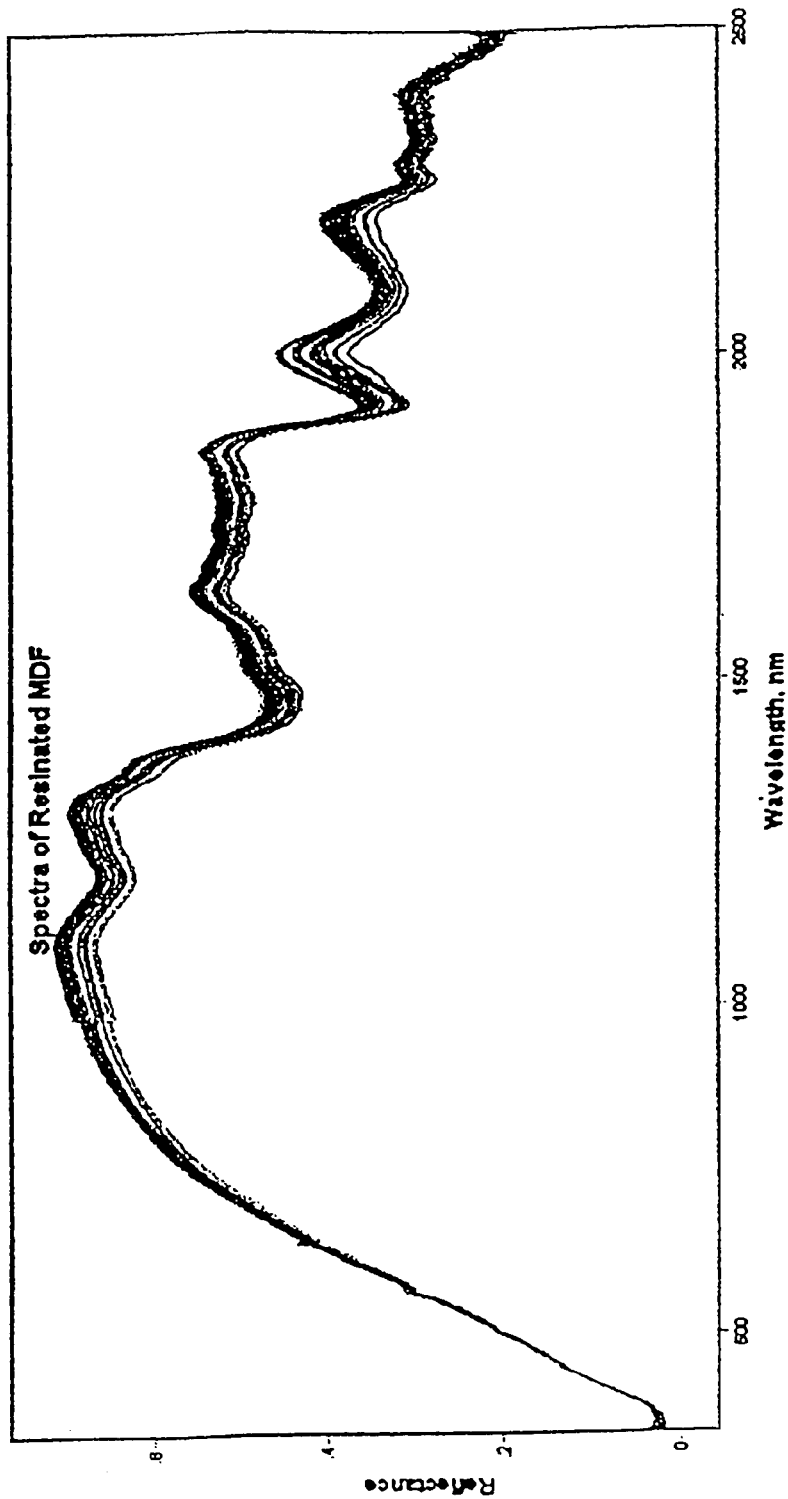

FIG. 6 shows the spectra obtained for different resin-loadings, and at different moisture contents, for resinated MDF fibers. Calibration based on actual pre-established resin-content, and the measured VIS/NIR absorption at selected differing wavelength ranges in the 400–2200 nm region resulted in a linear calibration curve as shown in FIG. 7, which includes water absorption wavelengths.

Figure 7:
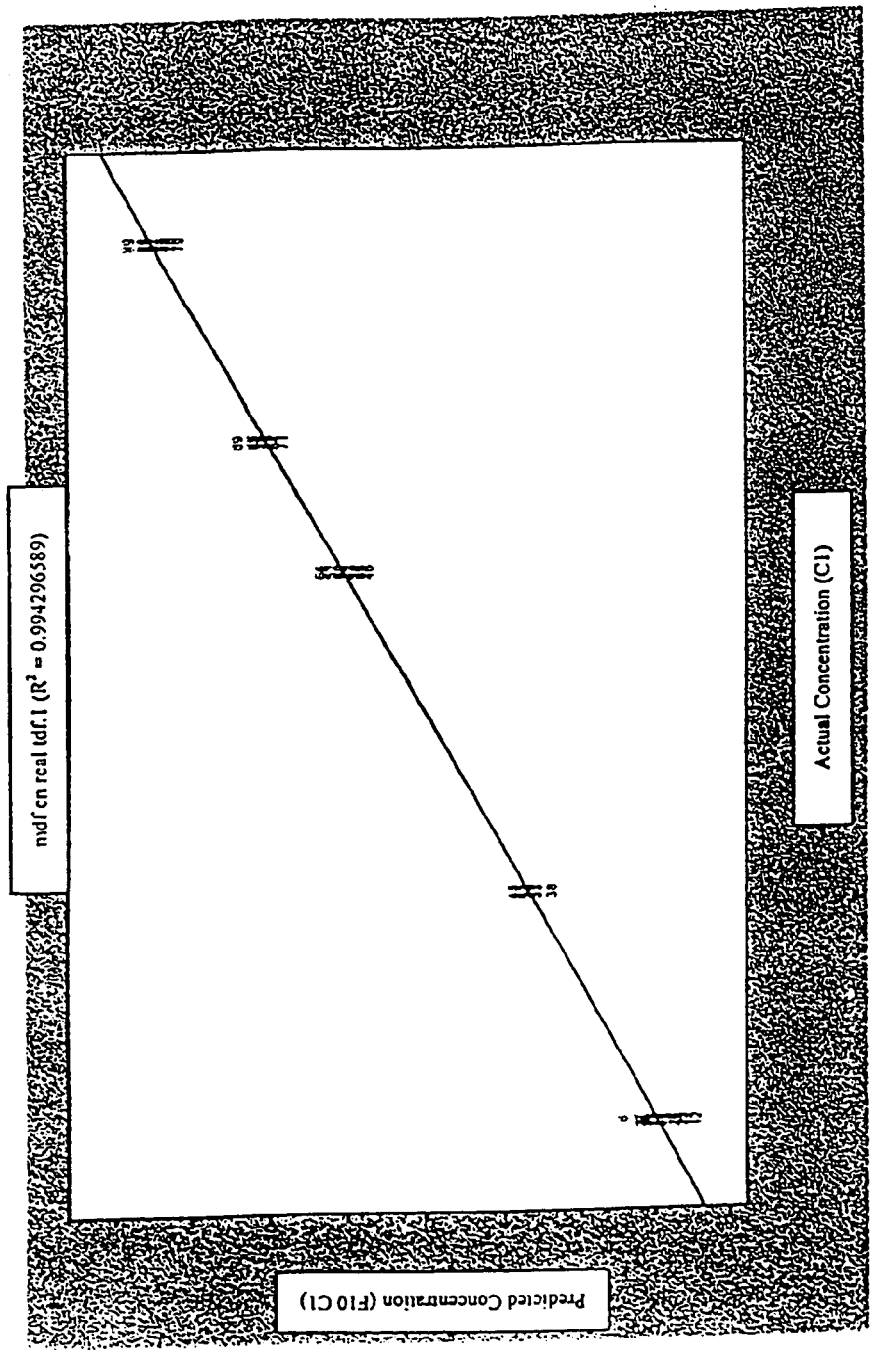
Figure 8:
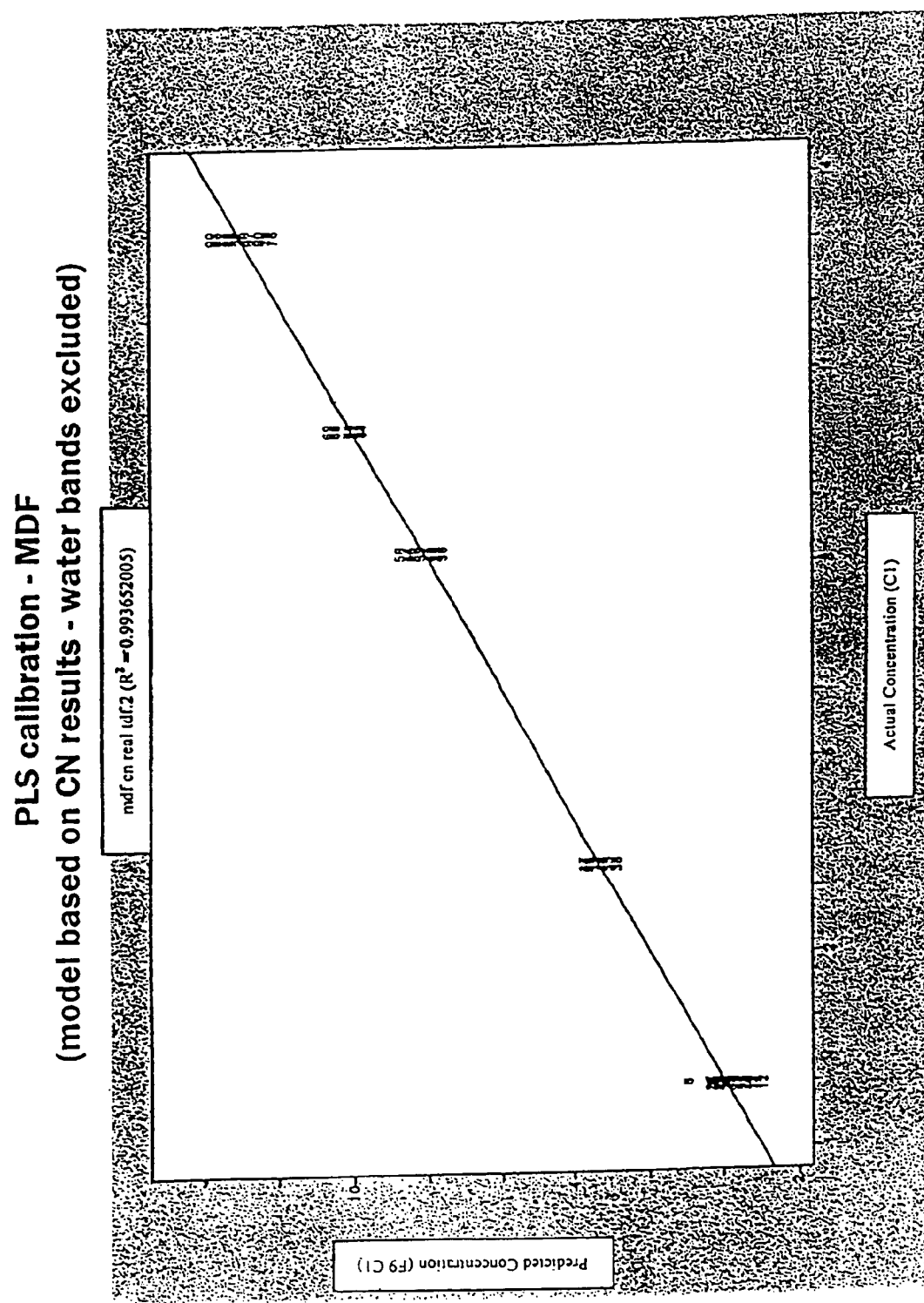

Calibration based on resin absorption, by excluding water absorption wavelength regions of 900–1000 nm, 1400–1450 nm and 1900–1950 nm, is shown in FIG. 8, which is substantially identical to FIG. 7. FIG. 8 shows that moisture content of the wood material, or of the resin, does not have significant effect on resin-loading measurements. Those results eliminate concern with water/moisture content of the substrate, environment, or the like, for effecting monitoring of the resin-content. Also, measurements in accordance with the invention are independent of wood type; the wood is a constant since the changes, if any, being measured are only with respect to the amount of resin.

The resin is selected in a fluid, preferably liquid, state so as to facilitate atomizing for fluidized bed application; some powdered resin can be used provided atomized fluidization is not disturbed. Wax, for water resistance of the composite product, and some other additives, can also be utilized with furnish-type wood materials; provided they can be added without disturbing desired atomizing for the resin-loading fluidized-bed operation of the invention.

Monitoring and measuring processes can also be carried out either including or excluding the wavelength regions measuring moisture content of the resin or wood materials, i.e., 900–1000 nm, 1400–1450 nm and 1900–1950 nm. Accurate results are obtained in absence of measurement of the water wavelength bands.

Spectroscopic Equipment
  Source:
  Analytical Spectral Devices, Inc. (ASD)
  5335 Sterling Drive, Suite A
  Boulder, Colo. 80301
Instrument Name: FIELDSPEC PRO.

| SENSORS (Arranged in Increasing Order of Price) | |
|---|---|
| Wavelength (nm) | Detection Type |
| 350–1050 | Silicon |
| 1000–1800 | Indium-Gallium-Arsenide; single spectrometer |
| 1000–2500 | Indium-Gallium-Arsenide; dual spectrometer |
| 350–2500 | Silicon + Indium-Gallium-Arsenide (photodiode array) |
| Source: Foss-NIR Systems | |
| 400–2500 | Lead Sulfide |

Software Processing Equipment
  Source: ASD
For collecting spectra data
Name: LabSpec PRO, version 6.0
For measured Data Processing
Name: Grams/32 V5

Resin
  Type: Urea Formaldehyde (UF)
Name: CHEMBOND® 5560
Source: Dynea, USA
  1600 Valley River Drive
  Suite 3900
  Eugene, Oreg. 97401

Detailed information on materials, values, apparatus and software have been described for purposes of disclosing the invention. However, the above disclosure can position others to make modifications in those specifics, without departing from the valid scope of protection of the present invention; therefore, the scope of patent protection should be determined from the appended claims, interpreted in the light of the above disclosure.

What we claim as our invention is:

1. Process utilizing electromagnetic-radiation spectroscopic instrumentation for quantitatively measuring resin application to raw wood-material furnish prior to heating and pressurized curing of said resin, for producing composite-panel wood-product, comprising
  (A) providing spectroscopic instrumentation, including
    (i) a visible-light spectrum lamp for illuminating resin-loaded wood-material furnish within a selected wavelength of or within a range of 350–2500 nm for penetration of the resin-loaded wood-material furnish, and
    (ii) sensor means responsive to electromagnetic radiation within said selected wavelength range;
  (B) calibrating said spectroscopic instrumentation so as to enable non-invasive quantitative measurement of resin-content of wood-material furnish while moving at a selected rate; by
  (C) verifying that a linear-relationship exists between:
    (i) quantitative percentage weight of applied resin to said wood-material furnish, and
    (ii) quantitative absorption of radiation in said selected wavelength range; which includes the steps of
      (a) accurately pre-establishing percentage weight of applied-resin on reference test-samples of raw wood-material furnish of a type selected for use in composite wood-product manufacture, with
      (b) said applied-resin being selected to be capable of curing, by heating and pressurizing, for bonding said furnish into an integral composite wood-product; and, further including
  (D) applying said resin to said reference test samples so as to establish an incrementally-increasing resin-content percentage weight for said raw wood-material test-samples, in which
    (i) said percentage weight of resin to weight of raw wood-material furnish, for respective test samples, varies by designated increments within a range from above zero percent (0%) to above about twelve percent (12%),
    (ii) supporting said pre-established resin-loaded test-samples on a conveyance surface positioned for irradiation within said selected range of wavelengths and so as to enable measuring non-absorbed radiation, reflected by said selected wood-material furnish test-samples, for indicating percentage weight of applied-resin to said respective reference-test samples,
    (iii) establishing a controlled rate of relative movement for said test-samples simulating a controlled rate of movement, for said type of resin-loaded wood-material furnish, typically used for in-line assembly,
    (iv) illuminating said pre-established resin-content test-samples with said visible-light spectrum lamp, within said selected range of wavelengths, during said controlled-rate relative movement so that a red portion of said visible light is absorbed by resin-content of said wood materials,
    (v) measuring non-absorbed radiation, reflected by said test-samples, for calibrating said spectroscopic instrumentation, with
      (a) said measured non-absorbed radiation, within said selected range of wavelengths, as reflected by said exposed test-samples during said relative movement, being graphically plotted versus (b) said pre-established percentage weight of applied-resin, as varying by said designated increments on said test-samples, for verifying (c) that said instrumentation, as calibrated, provides a linear relationship, between (d) percentage-weight of applied resin and (e) absorbed radiation by said applied resin, (f) enabling utilization of said instrumentation for measuring resin content of furnish, during in-line assembly, of said selected composite wood-product.

2. Process utilizing electromagnetic-radiation spectroscopic instrumentation for quantitatively measuring resin application to raw wood-material furnish prior to heating and pressurized curing of said resin, for producing composite-panel wood-product, comprising (A) providing spectroscopic instrumentation, including
  (i) source means for electromagnetic radiation within a selected wavelength range for penetration of resin-loaded wood-material furnish, and
  (ii) sensor means responsive to electromagnetic radiation within said selected wavelength range;

(B) calibrating said spectroscopic instrumentation so as to enable non-invasive quantitative measurement of resin-content of wood-material furnish while moving at a selected rate; by (C) verifying that a linear-relationship exists between:
  (i) quantitative percentage weight of applied resin to said wood-material furnish, and
  (ii) quantitative absorption of radiation in said selected wavelength range; which includes the steps of
    (a) accurately pre-establishing percentage weight of applied-resin on reference test-samples of raw wood-material furnish of a type selected for use in composite wood-product manufacture, with
    (b) said applied-resin being selected to be capable of curing, by heating and pressurizing, for bonding said furnish into an integral composite wood-product; and, further including (D) applying said resin to said reference test samples so as to establish an incrementally-increasing resin-content percentage weight for said raw wood-material test-samples, in which
  (i) said percentage weight of resin to weight of raw wood-material furnish, for respective test samples, varies by designated increments within a range from above zero percent (0%) to above about twelve percent (12%)
  (ii) supporting said pre-established resin-loaded test-samples on a conveyance surface positioned for irradiation within said selected range of wavelengths and so as to enable measuring non-absorbed radiation, reflected by said selected wood-material furnish test-samples, for indicating percentage weight of applied-resin to said respective reference-test samples,
  (iii) establishing a controlled rate of relative movement for said test-samples simulating a controlled rate of movement, for said type of resin-loaded wood-material furnish, typically used for in-line assembly,
  (iv) irradiating said pre-established resin-content test-samples, within said selected range of wavelengths, during said controlled-rate relative movement,
  (v) measuring non-absorbed radiation, reflected by said test-samples, for calibrating said spectroscopic instrumentation, with
    (a) said measured non-absorbed radiation, within said selected range of wavelengths, as reflected by said exposed test-samples during said relative movement, being graphically plotted versus
    (b) said pre-established percentage weight of applied-resin, as varying by said designated increments on said test-samples, for verifying
    (c) that said instrumentation, as calibrated, provides a linear relationship, between
    (d) percentage-weight of applied resin and
    (e) absorbed radiation by said applied resin,
    (f) enabling utilization of said instrumentation for measuring resin content of furnish, during in-line assembly, of said selected composite wood-product; and further including utilizing a full visible-light spectrum lamp for illuminating said test-samples, from which the red portion of said visible light is absorbed by resin-content of said wood-materials, and (E) selecting a wavelength range from the group consisting of:
  (i) 350–1050 nm,
  (ii) 1000–1800 nm,
  (iii) 1000–2500 nm, and
  (iv) 400–2500 nm.

3. The calibrating method of claim 2, capable of being carried out independently of an assembly line, comprising (F) establishing said controlled-rate of relative-movement for exposure of said test-samples to said radiation source and sensing non-absorbed radiation by said instrumentation, by (G) selecting a rotatable conveyance support-surface capable of being driven at a controlled rotational rate, so as to enable
  (i) simulating a typical controlled-rate of movement of said selected type of wood-material furnish during in-line assembly, and
  (ii) measuring, at that rate, reflected non-absorbed radiation from wood material furnish of said designated incrementally-varying applied-resin percentage-weights of said reference-test-samples, so as to
  (iii) verify said linear quantitative relationship between applied-resin and non-absorbed radiation as reflected by respective test-samples.

4. The process of claim 3, including selecting a wavelength range of about 400 nm to about 2250 nm, and (H) removing moisture-content absorptive effect from said non-absorbed reflected energy, by removing measurements at wavelengths of:

900 nm to 1000 nm, 1450 nm to 1500 nm, and 1900 nm to 2000 nm.

5. Calibrating spectroscopic instrumentation, as set forth in claim 3 in which (i) raw wood material furnish is selected from the group consisting of
  (a) wood-particulate, and
  (b) wood-fiber, for
(ii) verifying calibration of said instrumentation for in-line assembly of said selected raw wood-material furnish.

6. Process utilizing spectroscopic instrumentation, calibrated in accordance with claim 5, for assembly-line measurement of applied-resin, including
(H) designating an in-line location for said calibrated spectroscopic measuring instrumentation, providing for
  (i) non-invasive measuring of resin-content of selected wood-material furnish while moving in said assembly line, prior to
  (ii) subsequent heating and pressurizing curing of said applied resin, for
  (iii) bonding said wood-material furnish and producing integral-panel composite wood-product;
(I) selecting said raw wood-material furnish for producing said composite integral-panel wood-product, from the group consisting of
  (i) particulate for producing particleboard (PB), and,
  (ii) fibers for producing medium-density-fiber-board (MDF);
(J) controlling resin-loading of said selected wood material furnish in-line, by atomizing said resin and selecting from the group consisting of
  (i) quantitatively-controlling metering of said atomized resin for blending with said selected raw wood-material furnish, while said furnish is moving through said fluidized-bed of atomized resin,
  (ii) quantitatively controlling rate of movement of said raw wood material furnish moving through said fluidized-bed, and
  (iii) combinations of (i) and (ii); and, further including
(K) establishing a rate of in-line movement for said wood material furnish which is correlated with said rate of movement utilized during said calibration of said spectroscopic instrumentation for measurement of resin-loading, while
(L) measuring resin-content of said resin-loaded wood-material furnish, with such measuring being carried out, subsequent to delivery from said resin-loading fluidized-bed, while supported with respect to said instrumentation for irradiation and measuring radiation absorbed by said applied resin.

7. The process of claim 6, further including
(M) providing for quantitatively-controlling resin-loading of said selected raw wood material furnish during continuing in-line assembly, by
  (i) indicating resin-content as measured by said calibrated instrumentation, for
  (ii) providing feedback control of resin-loading, by
  (iii) selecting from the group consisting of
    (a) quantitatively controlling metering of resin into said fluidized-bed for contact with said selected raw wood-material furnish,
    (b) controlling rate of movement of said raw wood-material furnish through said fluidized-bed for delivery onto said assembly line, and
    (c) combinations of (a) and (b), for
  (iv) maintaining a desired uniform resin-content weight in relation to weight of said wood-materials during in-line assembly; then
  (v) curing said furnish applied-resin by timed exposure to heat and pressure, so as to
  (vi) bond said controlled applied-resin and said raw wood-material furnish for producing said integral composite wood product.

8. The process of claim 7, in which
wood-fiber furnish is selected for assembly into medium-density fiberboard (MDF); including the steps of
  (i) fluffing said wood-fiber furnish for applying said fluidized-resin, then
  (ii) compacting said resin-loaded wood fibers, as delivered from said fluidized-bed, forming a mat thickness for facilitating desired penetration of said compacted-fiber mat by said selected wavelength radiation, for measuring applied resin-content of said fibers.

9. Product-by-process composite-wood-product, produced by:
the process of claim 8 to produce integral-panel composite-medium-density fiberboard (MDF).

10. Product by process composite-wood product, produced by the process of claim 7, in which
particulate wood-material furnish is selected to produce integral composite-wood particleboard (PB).

* * * * *